United States Patent [19]
Kohtz

[11] Patent Number: 5,807,999
[45] Date of Patent: Sep. 15, 1998

[54] MONOCLONAL ANTIBODY THAT DISTINGUISHES BETWEEN PHOSPHORYLATED AND NONPHOSPHORYLATED HISTONE H1 AND USES THEREFOR

[75] Inventor: D. Stave Kohtz, New York, N.Y.

[73] Assignee: Mt. Sinai School of Medicine of the City University of New York, New York, N.Y.

[21] Appl. No.: 12,096

[22] Filed: Feb. 1, 1993

[51] Int. Cl.$^6$ .......................... C07K 16/00; G01N 33/53
[52] U.S. Cl. ..................... 530/387.1; 530/387.3; 530/388.2; 530/391.3; 435/7.1; 435/326
[58] Field of Search ............... 530/387.3, 388.2, 530/391.3; 435/240.2, 240.27

[56] References Cited

U.S. PATENT DOCUMENTS 5,225,325   7/1993   Miller et al. .

FOREIGN PATENT DOCUMENTS 2241782A   9/1911   United Kingdom ................. 33/53

OTHER PUBLICATIONS

Bers et al., Bigkhimiia 44:993–1001, 1979.
Sevier et al., Clin Chem, 27:1797–1806, 1981.
Morrison, Science 229:1202–1207, 1985.
Sternberger et al., "Aberrant neurofilament phosphorylation in Alzheimer disease," Proc. Natl. Acad. Sci. USA, 82:4274–4276, (1985).
Cole et al., "Growth Factors That Repress Myoblast Differentiation Sustain Phosphorylation of a Specific Site on Histone H1," J. of Biol. Chem., 268(3) : 1580–1585, (Jan. 25, 1993).
Fasy et al., "Phosphorylation of H1 and H5 Histones by Cyclic AMP–Dependent Protein Kinase Reduces DNA Binding," Biochimica et Biophysica Acta, 564:322–334, (1997).
Monestier et al., "Monoclonal Anti–Histone H1 Autoantibodies From MRL 1pr/1pr MICE," Molecular Immunology, 26(8) :749–758, (1989).
Ajairo, Kozo, et al., "Subtype–specific Cyclic AMP–dependent Histone H1 Phosphorylation at the Differentiation of Mouse Neuroblastoma Cells," J. Biological Chemistry, 265(11) :6494–6500 (1990).
Muller, S. et al., "Use if histone antibodies for studying Chromatin topography and the phosphorylation of chromatin subunits," EMBO Journal, 3(10) :2431–2436 (1984).

*Primary Examiner*—Lila Feisee
*Assistant Examiner*—Minh-Tam Davis
*Attorney, Agent, or Firm*—Hamilton, Brook, Smith & Reynolds, P.C.

[57] ABSTRACT

The present invention relates to: 1) A monoclonal antibody (mAb) that binds selectively to phosphorylated histone H1 and not to nonphosphorylated histone H1 and its use. In one embodiment, the mAb of the present invention binds selectively to histone H1 phosphorylated at the 12D11 epitope as defined herein, and 2) A cell producing a monoclonal antibody which binds selectively to phosphorylated histone H1 and has been shown to distinguish between histone H1 phosphorylated at the 12D11 epitope and histone H1 nonphosphorylated at this epitope.

14 Claims, 1 Drawing Sheet

MONOCLONAL ANTIBODY THAT DISTINGUISHES BETWEEN PHOSPHORYLATED AND NONPHOSPHORYLATED HISTONE H1 AND USES THEREFOR

GOVERNMENT SUPPORT

Work described herein was made with Government support under Grants HL40659 and HL43583 awarded by the National Institutes of Health. The Government has certain rights in the invention.

BACKGROUND

Cancer can arise in any of an individual's tissues, originating from practically any cell type. Cancer has, indeed, been said to be unique to the individual. This great diversity among human cancers has confounded efforts to develop widely applicable, reliable methods to detect cancer in its early stages, and to develop effective therapeutic agents for cancer, despite intensive research and development efforts over many years. With time, the general view has emerged that cancer is the manifestation of a loss, at the cellular or subcellular level, of identity as normal cells or tissue. The great physical and biochemical differences among all the tissue types found within an individual have, however, restricted the development of agents that can detect this change to reagents that can be used only for a single (or a closely related group) of tissue types. A need exists for a cancer-detection agent of wide applicablity to the many types of tissue found within an individual, from which cancer may arise.

SUMMARY OF THE INVENTION

The present invention relates to a monoclonal antibody (mAb) that binds selectively to phosphorylated histone H1 and not to nonphosphorylated histone H1 and its use.

In a first aspect, the invention relates to a mAb that distinguishes between phosphorylated histone H1 and nonphosphorylated histone H1. This is accomplished by employing a mAb that binds selectively to histone H1 that is phosphorylated at a specific site. The invention may also be practiced with a monoclonal antibody that binds selectively to histone H1 that is nonphosphorylated at the specific site. Preferably, selective binding is to histone H1 of human origin.

In one embodiment, the mAb of the present invention binds selectively to histone H1 phosphorylated at the 12D11 epitope as defined herein. It has been discovered that phosphorylation of histone H1 at this epitope diminishes in cells as differentiation progresses, and reaches a minimum coincident with the onset of terminal differentiation. Cells are said to have become terminally differentiated when they have acquired their final identity as normal cells of a particular tissue type (e.g., muscle, nerve, superficial cervical epithelium). These cells can no longer form tissue of another type, nor can they return to a less differentiated state. Moreover, the capacity for further growth (proliferation) is lost upon terminal differentiation. Certain types of normal tissue, however, retain sufficient proliferative capacity to allow for tissue turnover or renewal (e.g., blood producing stem cells in bone marrow).

As reported herein, the 12D11 epitope of histone H1 is dephosphorylated upon terminal differentiation. Conversely, terminal differentiation does not occur while the 12D11 epitope remains phosphorylated, although cells may enter a resting state (quiescence). Thus, the present mAb can be used to determine whether or not cells are terminally differentiated.

Tumors (also called neoplasms or carcinomas) are the manifestations of an abnormal loss, at the cellular or subcellular level, of identity as normal cells or tissue. Tumors may also arise from the failure of normal proliferating cells to properly differentiate and cease dividing. Thus, cancer is frequently associated with an aberrant return from a terminally differentiated state to a less differentiated state in which cells lose their final identity and regain the ability to proliferate. Cancer is also associated with an abnormal arrest of normal differentiation or tissue turnover processes. These phenomena are referred to herein as dedifferentiation, a term which is meant to include abnormal nondifferentiation. The present mAb may thus be used to assess tissue derived from an individual for the presence of dedifferentiated cells, and thereby for precancerous, dysplastic, preneoplastic, condyloma associated, neoplastic or cancerous changes according to the method described more fully below. A wide variety of tissue types, for example, muscle, thyroid, bladder, cervix, skin or blood, may be examined in this manner.

Preferably, the monoclonal antibody of the present invention is mAb 12D11, disclosed herein and also referred to as mAb PH-1. That is, the invention relates to an immunoglobulin having the epitope binding characteristics of mAb 12D11 as reported herein. Put differently, the invention relates to an immunoglobulin (e.g., a monoclonal antibody or a polyclonal antibody) that binds to the 12D11 epitope of phosphorylated histone H1. It must be understood that the 12D11 epitope may be present in intact histone H1, or may be present in a portion or fragment thereof (e.g., a tryptic peptide of H1), optionally attached to a carrier molecule (e.g., keyhole limpet hemocyanin), or in a recombinant protein in which the 12D11 site of H1 is joined to another polypeptide (e.g., $\beta$-galactosidase). In essence, the invention may be viewed as relating to the heavy-chain and light-chain regions of monoclonal antibody 12D11 that are necessary and sufficient for binding to the 12D11 epitope. These regions are meant to include the regions of mAb 12D11 that are directly involved in epitope binding together with any framework regions that provide support or maintain the configuration of epitope-binding regions.

In a second aspect, the present invention relates to a cell producing a monoclonal antibody which binds selectively to phosphorylated histone H1 and has been shown to distinguish between histone H1 phosphorylated at the 12D11 epitope and histone H1 nonphosphorylated at this epitope. Preferably, the monoclonal antibody produced by the cell binds selectively to phosphorylated histone H1 of human origin. The cell can be a hybridoma cell or a recombinant cell. Thus, the present invention encompasses immortalized hybridoma or recombinant cell lines. These immortalized cell lines include the molecular components necessary and sufficient for producing a mAb with the epitope binding characteristics of mAb 12D11 (e.g., nucleic acid fragments comprising regions that encode the heavy and light chain portions of immunoglobulin 12D11 (or fragments thereof needed for binding to the 12D11 epitope of histone H1), together with a promoter and other nucleic acid elements needed for expression; intracellular proteins, including enzymes, needed for transcription, translation, processing and assembly of a functioning immunoglobulin). That is, the invention relates to a hybridoma or recombinant cell line producing an immunoglobulin, or a polypeptide chain or fragment thereof, that binds to the 12D11 epitope of phosphorylated histone H1. In preferred embodiments, the immunoglobulin is mAb 12D11.

In another aspect, the present invention relates to a method for evaluating cells or tissue obtained from an individual for the presence of dedifferentiated (or nondifferentiated) cells. Cells are treated to render nuclear proteins accessible for binding with, e.g., pepsin or a low-pH wash solution. The treated cells are combined or contacted with an immunoglobulin that distinguishes between phosphorylated histone H1 and nonphosphorylated histone H1 as described above. Preferably, this immunoglobulin binds selectively to phosphorylated histone H1. The treated cells are incubated with the immunoglobulin under conditions sufficient for the binding of the immunoglobulin to phosphorylated histone H1 (i.e., immunological binding conditions). Binding of the immunoglobulin to phosphorylated histone H1 is then detected, and the extent of immunoglobulin binding is evaluated relative to the binding of the immunoglobulin to normally differentiated cells of comparable type which have been treated in a similar manner.

The cells upon which the method described herein is carried out can be cultured cells, or in many embodiments, can be primary cells obtained from an individual. Cells can be obtained from an individual in the form of a cell suspension in a biological fluid (e.g., blood, urine, cerebrospinal fluid), or may be present in tissue samples or specimens. Thus, cells or tissue may be in the form of a surgically resected pathology specimen, or of a presurgical biopsy or cytologic specimen (e.g., a PAP smear). The above method may be practiced by extracting or purifying phosphorylated histone H1 from cells, e.g., by electrophoretic resolution of proteins from lysed cells. Alternatively, phosphorylated histone H1 can be examined in situ, in cells or tissue samples (e.g., sections mounted on surfaces suitable for microscopic viewing) that have been treated to allow access to nuclear proteins by immunological reagents. In certain embodiments, binding is detected by immunofluorescence, immunohistochemistry or immunocytochemistry. Alternatively, the binding of a radiolabelled immunoglobulin can be detected by autoradiography.

Kits are also the subject of the present invention and are suitable for practicing the method discussed above. Generally, the present kits include a monoclonal antibody that distinguishes between histone H1 phosphorylated at the 12D11 epitope and histone H1 nonphosphorylated at 12D11 epitope, and reagents for detecting the monoclonal antibody once it is bound to the 12D11 epitope of phosphorylated histone H1. Preferably, the monoclonal antibody binds selectively to histone H1 phosphorylated at the 12D11 epitope. In one embodiment the monoclonal antibody is 12D11. Optionally, reagents (pepsin, dilute hydrochloric acid) for treating cells or tissue to render nuclear proteins accessible for immunological binding may also be included, as may immunofluorescent detection reagents (an anti-immunoglobulin antibody derivatized with fluorescein or rhodamine, or a biotinylated anti-immunoglobulin antibody together with avidin or streptavidin derivatized with fluorescein or rhodamine), immunohistochemical or immunocytochemical detection reagents (an anti-immunoglobulin antibody derivatized with alkaline phosphatase or horseradish peroxidase, or a biotinylated anti-immunoglobulin antibody together with avidin or streptavidin derivatized with alkaline phosphatase or horseradish peroxidase). In one embodiment, the kit includes one or more reagents for immunoperoxidase staining (an anti-immunoglobulin antibody derivatized with horseradish peroxidase, or a biotinylated anti-immunoglobulin antibody together with avidin or streptavidin derivatized with horseradish peroxidase), together with a chromogenic substrate therefor (e.g., diaminobenzidine).

In one embodiment, a kit of the present invention includes nonphosphorylated H1, phosphorylated H1 or both on a solid support, such as a plate; optionally, cdc2 or cdk2 enzyme and an appropriate inhibitor; 12D11 monoclonal antibody and, optionally an antio-HRP antibody.

DETAILED DESCRIPTION OF THE INVENTION

Figure 1A:
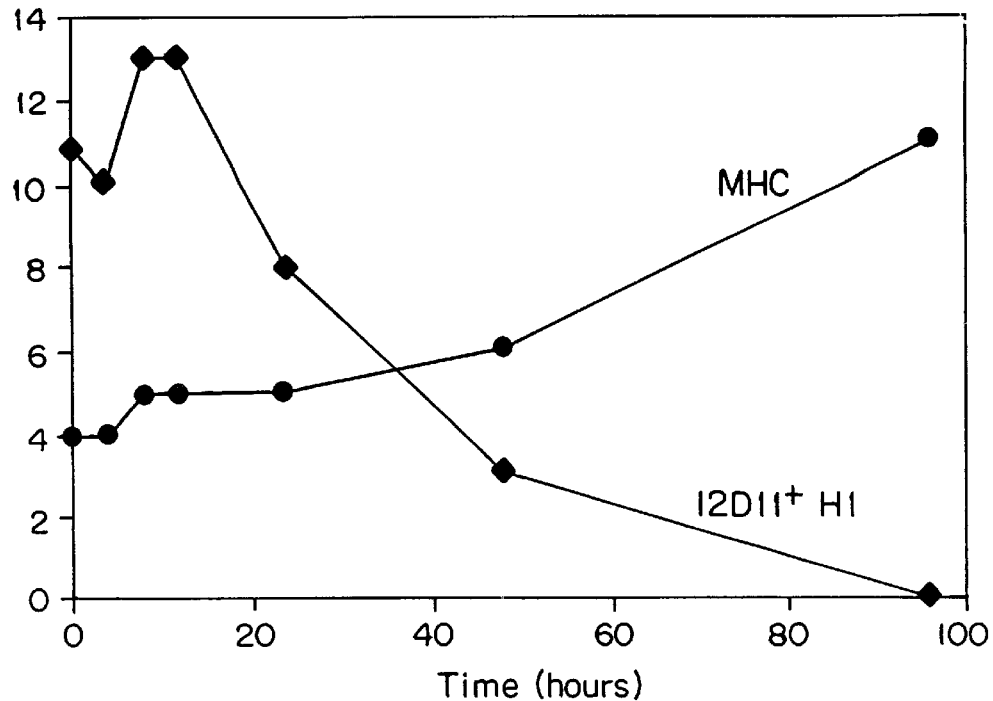
FIG. 1A is a schematic illustration of a microdensitometry scan of Western-blotted timecourse samples assessing the onset of differentiation in HUSK cells. MHC, reactivity of blotted cellular proteins with reference mAb MF-20. $12D11^+$ H1, reactivity of blotted cellular proteins with mAb 12D11.

The invention disclosed herein is based upon the discovery and characterization of a monoclonal antibody (mAb) that distinguishes between phosphorylated histone H1 and nonphosphorylated histone H1. This mAb, called 12D11 or PH-1, binds selectively to histone H1 only when H1 is phosphorylated at a specific site, referred to as he 12D11 epitope. Thus, phosphorylated histone H1 to which mAb 12D11 can bind is identified herein as $12D11^+$ H1.

Generally, the invention presently disclosed relates to an immunoglobulin that binds to the 12D11 epitope of phosphorylated histone H1, to cells (including immortalized cell lines, e.g., hybridoma cell lines) producing an immunoglobulin that binds to the 12D11 epitope, to methods for using this immunoglobulin to assess the onset or loss of terminal differentiation in cells, and to kits containing reagents needed for the practice of the methods described herein. In certain embodiments, the immunoglobulin is mAb 12D11, a monoclonal antibody comprised of murine $\mu$ heavy chains and murine $\kappa$ light chains. The essence of the invention, however, lies within the portions of mAb 12D11 heavy and light chains that are necessary and sufficient for epitope binding. Thus, the present invention encompasses any protein, such as an immunoglobulin or epitope-binding fragment thereof, that binds to the 12D11 epitope of phosphorylated histone H1. Such proteins, immunoglobulins or fragments would include fragments of mAb 12D11 obtained by pepsin or papain digestion, isotype switched derivatives of mAb 12D11, recombinant chimeric antibodies derived from mAb 12D11 and comprising the heavy chain and/or light chain constant regions of other immunoglobulin isotypes or other biological species (e.g., mouse, rat, hamster, human), recombinant 12D11 polypeptide chains produced by bacterial expression, polyclonal antisera which bind selectively to $12D11^+$ H1, and the like.

mAb 12D11 can be used according to the methods described herein for assessing the differentiation state of cells or tissue. mAb 12D11 reactivity in cells or tissue obtained from an individual may be indicative of cancerous or precancerous changes. In certain embodiments, phosphorylated histone H1 may be assessed in situ, in the nuclei of cells or tissue treated so as to allow immunological binding to nuclear proteins. Immunofluorescent, immunocytochemical or immunohistochemical methods may be used; immunoperoxidase staining is preferred. Alternatively, a radiolabelled anti-$12D11^+$ antibody may be used, and reactivity in situ visualized by autoradiography.

Phosphorylated histone H1 may also be assessed in cell lysates, cell extracts, subcellular fractions (e.g., nuclear extracts) or in purified form. Thus, histone H1 can be electrophoretically resolved (e.g., by sodium dodecyl sulfate-polyacrylamide gel electrophoresis) and transferred by Western blotting to a surface suitable for immunological binding (e.g., a nitrocellulose sheet). Electrophoretic resolution is not always necessary; it may be desirable to adsorb histone H1 directly to a surface suitable for immunological binding. This surface may be, e.g., a multi-welled plate for enzyme linked immunosorbent assay, a nitrocellulose sheet for dot or slot blot assay, or the like. Alternatively, histone H1 can be assessed in solution, e.g. by competition with radiolabelled histone H1.

mAb 12D11 reactivity can be detected directly or indirectly. That is, mAb 12D11 may be detectably labeled, or may be bound by detectably labeled immunological or other reagents. More specifically, mAb 12D11 may be derivatized with a radioisotope, a fluorophore, a chromophore, a metal atom, a hapten, a chemical crosslinking agent, biotin, avidin, streptavidin, a receptor ligand, a receptor, or an enzyme. In certain embodiments, mAb 12D11 reactivity may be detected using further immunological or other reagents, including a second antibody (an anti-immunoglobulin antibody) optionally linked to an enzyme, biotin or a radioisotope; avidin or streptavidin that has been similarly derivatized; or a commercially available avidin-biotin amplification system linked to an enzyme (e.g., Vectastain ABC, a kit available from Vector Laboratories, Inc.). Preferred enzymes include alkaline phosphatase and horseradish peroxidase; peroxidase is employed in many of the studies discussed herein. There are many enzyme substrates which produce chromogenic reaction products which can be used in the present invention. Diaminobenzidine is one peroxidase substrate employed herein.

The kits provided herein include the monoclonal antibody of the present invention, together with reagents, such as the elements described above, for detecting the present monoclonal antibody. Optionally, these kits further include reagents for treating cells or tissue to render nuclear proteins accessible for immunological binding. Suitable reagents for this purpose include pepsin or a dilute acid to provide low pH, such as dilute hydrochloric acid.

These and other aspects of the preferred embodiments are described more fully below.

Relevance of Histone H1 Phosphorylation to the Control of Differentiation and Proliferation in Cells Differentiation of proliferating myoblasts into muscle is inhibited in culture by components of serum or embryo extracts. Konigsberg (1963), 140 SCIENCE 1273–1284; Konigsberg et al. (1978), 63 DEV. BIOL. 11–26; Slater (1976), 50 DEV. BIOL. 264–284. Some inhibitors have been identified as growth factors, and include basic fibroblast growth factor and transforming growth factor β (hereinafter TGF-β). Gospodarowicz et al. (1976), 70 J. CELL BIOL. 395–405; Linkhart et al. (1980), 14 J. SUPRAMOL. STRUCT. 384–498; Clegg et al. (1987), 105 J. CELL BIOL. 949–956; Olson et al. (1986), 103 J. CELL BIOL. 1799–1805; Massague et al. (1986), 83 PROC. NATL. ACAD. SCI. U.S.A. 8206–8210. Homogeneous preparations of these factors, either alone or in combination, inhibit differentiation of myoblasts in culture, and their subsequent removal results in spontaneous morphological and biochemical differentiation of the myoblasts into skeletal muscle fibers. Myoblasts cultured in low mitogen medium at confluence in the presence of TGF-β are mitogenically arrested but remain undifferentiated until the factor is removed (Olson et al. (1986), 103 J. CELL BIOL. 1799–1805.), indicating that inhibition of myogenic differentiation by TGF-β is not inextricably linked to its activity as a mitogen. The molecular mechanisms which determine that proliferating myoblasts will eventually differentiate into muscle, but defer differentiation until the ambient concentration of growth factors is reduced, are being actively investigated.

The discovery of myogenic determination genes, which when transfected and constitutively expressed in cells of other phenotypes induce trans-determination into myoblasts, has provided a focus for understanding the regulation of differentiation. Four distinct myogenic determination genes have been described: MyoD1 (Davis et al. (1987), 51 CELL 987–100.), myogenin (Wright et al. (1988), 56 CELL 607–617), myf-5 (Braun et al. (1989), 8 EMBO J. 701–709) and MRF4/myf-6/herculin (Rhodes and Koznieczny (1989), 3 GENES & DEV. 2050–2061; Braun et al. (1990), 9 EMBO J. 821–831; Miner and Wold (1990), 87 PROC. NATL. ACAD. SCI. U.S.A. 1089–1093). All four share a 68 residue DNA-binding motif referred to as a basic-helix-loop-helix (Murre et al. (1989), 56 CELL 777–783), also common to an extended family of transcription factors relevant to development. The myogenic determination proteins bind a consensus sequence found one or more times in the enhancer elements of muscle-specific genes (Buskin and Hauschka (1990), 9 MOL. CELL. BIOL. 2627–2640; Lassar et al. (1989), 59 CELL 823–831; Murre et al. (1989), 58 CELL 537–544; Lassar et al. (1991), 66 CELL 305–315), and thereby trans-activate transcription of these genes in differentiated myocytes. Since the expression of myogenic determination genes can occur either natively or through forced expression in undifferentiated myoblasts (which do not express most muscle-specific genes) as well as in differentiated myofibers, their ability to activate transcription of muscle-specific genes must be regulated so that these genes are expressed only in differentiated cells. In vivo footprint studies of the endogenous muscle creatine kinase gene enhancer have shown that the MyoD1 binding sequence is unoccupied in myoblasts while it is occupied in differentiated muscle fibers. Mueller and Wold (1989), 246 SCIENCE 780–786. It is unlikely that this difference is due to post-translational modifications of the MyoD1 protein, since MyoD1 isolated from myoblasts or from myofibers displays equivalent binding activity in gel shift assays. Lassar et al. (1989), 59 CELL 823–831; Lassar et al. (1991), 66 CELL 305–315. Regulation of MyoD1 activity may be explained by the modulating action of c-jun (or junB), which inhibits myogenesis (when overexpressed) and forms a complex with MyoD1 in vivo. Bengal et al. (1992), 68 CELL 507–519; Li et al. (1992), 6 GENES & DEV. 76–689. The results of the studies disclosed herein support the hypothesis of an alternate or additional regulatory mechanism, in which the accessibility of muscle-specific enhancers differs between myoblasts and differentiated myofibers.

It is now widely understood from in vitro studies that transcriptional repression by histone H1 constitutes a central mechanism for regulating eukaryotic gene expression. Histone H1 has been shown to repress transcription in vitro. See discussions in Weintraub (1985), 42 CELL 705–711 and Felsenfeld (1992), 355 NATURE 218–223. The ability of certain trans-activators to overcome this effect is referred to an anti-repression. Croston et al. (1991), 251 SCIENCE 643–649. Although many studies have indicated that histone H1 mediates the condensation of chromatin (Bradbury et al. (1974), 247 NATURE 257–261; Allan et al. (1980), 288 NATURE 675–679; Staynov and Crane-Robinson (1988), 7

EMBO J. 3685–3691), the mechanism by which histone H1 represses transcription in vitro is not yet clear. The addition of histone H1 to Xenopus chromatin in vitro has been observed to selectively repress oocyte 5 S RNA genes whereas somatic 5 S RNA genes remain transcriptionally active. Schlissel and Brown (1984), 47 CELL 903–914; Wolffe (1989), 8 EMBO J. 527–535. In this RNA polymerase III system, hyperphosphorylation of H1 by growth-associated H1 kinase decreased the potency of H1 as a transcriptional inhibitor. Jerzmanowski and Cole (1990), 265 J. BIOL. CHEM. 10726–10732. Others have shown that transcriptional repression by histone H1 in vitro does not necessarily require assembled chromatin as a template. Purified H1 is capable of repressing transcription from several naked DNA templates, including Drosophila jockey, alcohol dehydrogenase (proximal), Drosophila Ultrabithorax, Drosophila Kruppel, adenovirus major late, and E4 promoters. See Croston et al. (1991), 251 SCIENCE 643–649 and references cited therein.

Transcriptional repression by histone H1 is thought to result from inaccessibility of the compact higher order structures to transcriptional machinery. See detailed discussions by Weintraub (1985), 42 CELL 705–711 and Felsenfeld (1992), 355 NATURE 218–223. Compelling evidence has also been presented that histone H1 acts as a general repressor of transcription in the presence (Shimamura et al. (1989), 9 MOL CELL. BIOL. 5573–5584) or absence (Croston et al. (1991), 251 SCIENCE 643–649) of core histones. Activation of transcription by some DNA-binding proteins has been shown in vitro to be associated with their ability to prevent repression by histone H1; in this context, these transcription factors can be regarded as anti-repressors. Croston et al. (1991), 251 SCIENCE 643–649. Consistent with this hypothesis, studies in vivo have shown that H1 is repositioned or depleted from the promoter regions of some active or competent genes. Nacheva et al. (1989), 58 CELL 27–37. Moreover, histone H1 more efficiently inhibits transcription of *Xenopus laevis* oocytes 5 S RNA genes than it does somatic 5 S RNA genes, and the selectivity of this effect depends on the presence of A+T-rich flanking sequences in the oocyte gene. Jerzmanowski and Cole (1990), 265 J. BIOL. CHEM. 10726–10732. Taken together, these in vitro and in vivo studies indicate that the repressive effect of histone H1 may be essential for proper In vivo developmental regulation of the expression of certain genes.

Monoclonal Antibody (mAb) 12D11 Binds to Histone H1 only when Phosphorylated at the 12D11 Epitope New mAb 12D11 (also referred to as PH-1), disclosed herein, binds a phosphorylated subset of histone H1. Binding of mAb 12D11 is abolished by treating histone H1 with bacterial alkaline phosphatase. This antibody is a powerful and unique tool for in situ analysis of the phosphorylation state of a specific site on histone H1 to which mAb 12D11 binds; this site is hereinafter referred to as the 12D11 epitope. There is at least one 12D11 epitope in each molecule of histone H1. As discussed below, a prerequesite for 12D11 binding is that the 12D11 epitope be phosphorylated. Thus, histone H1 in which the 12D11 epitope is phosphorylated is referred to herein as 12D11$^+$ H1. Conversely, histone H1 in which the 12D11 epitope is not phosphorylated, to which mAb 12D11 does not bind, is referred to herein as 12D11$^-$ H1.

As reported herein, phosphorylation of histone H1 at the 12D11 epitope is observed at high levels in skeletal myoblasts, but is not observed in differentiated myocytes. Mitogenically arrested myogenic cells that are undifferentiated, such as quiescent mononuclear cells in differentiated cultures and myoblasts cultured in low mitogen medium supplemented with TFG-$\beta$, also maintain high levels of histone H1 phosphorylated at the 12D11 epitope (i.e., 12D11$^+$ H1). Evidence is presented herein that phosphorylation of histone H1 at the specific site(s) of mAb 12D11 binding is associated with regulation of myoblast differentiation. Phosphorylation at this site appears to be a downstream event which follows exposure to growth factors that inhibit myogenic differentiation, and thus this inhibition may be linked to the regulation of transcriptional repression.

More specifically, dephosphorylation of a specific epitope on histone H1 (the 12D11 epitope) is shown to be tightly associated with the induction of myogenic differentiation. To directly observe phosphorylation at this epitope, a novel histone H1 mAb (12D11) was used that binds the epitope only when it is phosphorylated. This approach avoids the artifacts and limitations associated with metabolic labeling experiments and permits analyses of the phosphorylation state of the epitope in individual nuclei in situ.

Phosphorylation of histone H1 at the 12D11 epitope was not found to be directly associated with replication of the cells, as both proliferating and nonproliferating undifferentiated cells displayed 1211$^+$ histone H1. In the presence of differentiation (low mitogen) medium supplemented with TGF-$\beta$, myoblasts withdraw from the cell cycle do not express most of the biochemical and morphological markers of differentiated skeletal myocytes. Olson et al. (1986), 103 J. CELL BIOL. 1799–1805. Quiescent myoblasts (murine C2C12 cells (Blau et al. (1983), 22 CELL 1171–1180) and primary human skeletal myoblasts, referred to as HUSK cells (Feghali et al. (1992), 2 GENE EXPRESSION 49–58), at confluence in low mitogen medium supplemented with TGF-$\beta$ displayed levels of 12D11$^+$ histone H1 that were as high as those of myoblasts proliferating in high mitogen medium. These observations further support the general consensus that different functions must be subserved by phosphorylation of different sites on histone H1, since total phosphorylation of histone H1, as determined by metabolic labeling, is usually higher in rapidly dividing cells than in nonproliferating and quiescent cells. Bradbury et al. (1974), 247 NATURE 257–261; Gurley et al. (1978), 84 EUR. J. BIOCHEM. 1–15; Ajiro et al. (1981), 20 BIOCHEMISTRY 1445–1454.

Most previous studies of histone H1 phosphorylation have been concerned with growth-associated phosphorylation sites, and only a few have considered that phosphorylation of histone H1 could regulate gene expression in response to extra-cellular factors and during cell differentiation. Liver-specific gene expression induced in vivo by glucagon has been shown to be positively associated with phosphorylation of histone H1 at serine 37. Hashimoto et al. (1984), 81 PROC. NATL. ACAD. SCI. U.S.A. 6637–6641. This residue is phosphorylated in vitro by the cAMP-dependent protein kinase. Langan (1968), 162 SCIENCE 579–580; Langan (1969), 64 PROC. NATL. ACAD. SCI. U.S.A. 1276–1283. Mouse N18 neuroblastoma cells, which are induced to differentiate by analogues of cAMP, also display isoform-specific phosphorylation of serine 37 in the initial phases of differentiation. Ajiro et al. (1990), 265 J. BIOL. CHEM. 6494–6500. Finally, regulation of histone H1 phosphorylation has been correlated with changes in gene expression in Tetrahymena induced by heat, starvation, and conjugation. Roth et al. (1988), 107 J. CELL BIOL. 2473–2482; Lin et al. (1991), 5 GENES & DEV. 1601–1610.

Dephosphorylation of a specific site on histone H1 (the 12D11 epitope) is shown herein to be linked to the morphological and biochemical differentiation of skeletal myoblasts. Treatment of confluent myoblasts in low mitogen medium with TGF-β inhibits differentiation but allows the cells to withdraw from the cell cycle (Olson et al. (1986), 103 J. CELL BIOL. 1799–1805), and results in levels of 12D11$^+$ histone H1 comparable to or exceeding those observed in proliferating myoblasts. These data clearly indicate that dephosphorylation of histone H1 at the 12D11 epitope is linked to differentiation of the myoblasts and that cessation of proliferation is not sufficient to induce differentiation or epitope dephosphorylation.

Since histone H1 is an abundant nuclear protein, modulation of its transcriptional repressive activity by phosphorylation is likely to affect the expression of large panels of genes. One possible model of how phosphorylation of histone H1 could regulate myogenic differentiation would entail differential sensitivity of muscle-specific promoters to repression by phosphorylated and unphosphorylated histone H1. In this model, housekeeping genes expressed in both myoblasts and myocytes would not distinguish between 12D11$^+$ and 12D11$^-$ histone H1, while myocyte-specific genes would be potently repressed by 12D11$^+$ histone H1, and/or myoblast-specific genes would be potently repressed by 12D11$^-$ histone H1. MyoD1 (Davis et al. (1987), 51 CELL 987–100) is a skeletal muscle-specific transcriptional activator that is expressed in equivalent forms in both skeletal myoblasts and differentiated myocytes. Binding sites for MyoD1 are found in the enhancers of several muscle-specific genes, and several studies have shown that these sites are required for expression of the genes in differentiated myocytes. Lassar et al. (1989), 59 CELL 823–831; Sartorelli et al. (1990), 4 GENES & DEV. 1811–1822. In vivo footprinting of the MyoD1 binding site in the endogenous muscle creatine kinase enhancer, however, has shown that it is unoccupied in myoblasts and occupied in differentiated myocytes. This result is consistent with the hypothesis that muscle-specific transcriptional activators present in both myoblasts and myocytes (in this case MyoD1) are not effective as anti-repressors of 12D11$^+$ histone H1 (present in myoblasts), whereas they are effective with 12D11$^-$ histone H1 (presence in myocytes). Therefore, the data presented herein are entirely consistent with a model of myogenic differentiation in which access of muscle-specific transcriptional activators to enhancer binding sites is regulated by the phosphorylation state of histone H1.

mAb 12D11 (PH-1) is Useful Generally to Distinguish between Proliferating, Quiescent and Differentiated Cells From the foregoing, it will be apparent that mAb 12D11 (PH-1) is a powerful tool for distinguishing between cells whose nuclei are rich in 12D11$^+$ histone H1 (i.e., H1 phosphorylated at the 12D11 epitope) and cells whose nuclei lack significant levels of 12D11$^+$ H1 (wherein the 12D11 epitope is not phosphorylated). It will further be apparent that the presence of appreciable levels of 12D11$^+$ H1 correlates with proliferative capacity, not simply active proliferation. Thus, mAb 12D11 is reactive with cells that are quiescent yet capable of proliferating. Conversely, nonphosphorylation of the 12D11 epitope, manifested as lack of reactivity with mAb 12D11, correlates with the onset of terminal differentiation which includes the onset of an irreversibly amitotic state.

In a healthy individual, many tissues have become terminally differentiated, or retain only sufficient proliferative capacity to allow normal tissue turnover or repair (e.g., skin, bone, blood). The loss of differentiation (dedifferentiation), or the failure to proceed normally to a fully differentiated state (nondifferentiation) is often accompanied by the release of cells from normal mechanisms which restrain proliferation. Dedifferentiation (which term is meant to include nondifferentiation) is thus indicative of cancer, and the degree of dedifferentiation correlates with clinical aggressiveness, as manifested by the rate of tumor growth and/or by the presence of metastases to other sites in the body. It should be noted that these events, dedifferentiation and release from growth control, do not always occur simultaneously. In some tissues, such as the cervix, dedifferentiation precedes the onset of malignant growth.

Protein phosphorylation is the biochemical attachment of one or more phosphate moieties to proteins (e.g., histone H1) at specific sites of the protein molecule. In vivo, phosphorylation is a tightly regulated event that is central to the activation or deactivation of numerous metabolic pathways which determine the behavior of cells, including pathologically activated pathways which can convert a normal cell into a cancer cell. It is known that histone H1 is closely associated with deoxyribonucleic acid (DNA) and that phosphorylation can affect the affinity of histone H1 for DNA. Chromatin, the form in which DNA is present in living cells, is a complex of DNA with several types of proteins, including significant levels of histone H1. Thus, association of DNA with, or release of DNA from, histone H1 is likely to be manifested as a general conformational change in chromatin. Such conformational changes may serve to initiate cell division, or to activate or deactivate specific genes or entire panels of genes. These changes in the overall pattern of cellular gene expression may lead to changes in cell function or metabolism, e.g., the acquisition or loss of identity as a terminally differentiated cell. By virtue of its unique ability to distinguish between two different phosphorylation states of histone H1, new mAb 12D11 makes possible the ready visualization of early cellular events in the genesis of cancer.

Toward this end, studies have been performed in which mAb 12D11 (PH-1) was employed as a primary antibody for immunohistochemistry studies in which the levels of 12D11$^+$ histone H1 present in cytologic preparations of a variety of human cancers were compared with preparations of normal counterpart tissue. As part of these studies, preparations of urothelial carcinoma of the bladder were compared to preparations of normal bladder cells. The nuclei of urethelial carcinoma cells exhibited more intense 12D11 reactivity (12D11-dependent immunoperoxidase staining) than benign urothelial cells. Benign squamous cells derived from the bladder lining showed essentially no reactivity. Differential staining patterns have also been obtained between carcinomas of diverse types and their tissues of origin, such as skin, cervical tissue from biopsies and thyroid tissue (thyroid and cervical studies are discussed more fully below). Other tissue or cell types that have been assessed include adult and embryonic cells of neuronal lineage, and hematopoetic cells. In peripheral blood, lymphocytes (which retain the capacity to proliferate upon appropriate stimulation) have been found to retain the 12D11 epitope, whereas this reactivity is lost in polymorphonuclear leukocytes (neutrophils). Neutrophils are known to be terminally differentiated, and are the cell type whose precursors undergo neoplastic change in chronic myelogenous leukemia (CML) or preneoplastic change in myelodysplasia (MD). CML and MD are diseases characterized by progressive dedifferentiation over an extended period, culminating in the onset of an aggressive hematopoetic neoplasm.

From the aforementioned studies, it has become apparent that new mAb 12D11 may be a tool of general applicability, not restricted to use in the diagnosis of cancerous changes in a single tissue type. Accordingly, mAb 12D11 (PH-1) is viewed as useful in assessing dedifferentiation, including both actively proliferative and quiescent states, in any tissues that are normally terminally differentiated in healthy individuals. Thus, in addition to its usefulness in assessing bladder, thyroid and cervical tissues for cancerous or precancerous changes, mAb 12D11 may additionally be useful in testing individuals for, e.g., the onset of chronic myelogenous leukemia or myelodysplasia. Additional applications of mAb 12D11 include monitoring individuals undergoing treatment for cancer (e.g., by chemotherapy or radiotherapy) for the possible reemergence of neoplasms, or to confirm that the disappearance of a preexisting neoplasm.

To carry out the present studies of cytologic preparations and other routine, surgically resected tissue specimens, it was necessary to develop an improved immunohistochemical/immunocytochemical method tailored for detecting phosphorylated histone H1 in situ. Initial attempts to apply standard immunoperoxidase techniques to archival, routinely processed surgical pathology sections failed to produce results with the clarity, consistency and reliabilty needed in a clinical diagnostic technique. This was not surprising, upon consideration that surgically resected specimens are routinely subjected to formaldehyde preservation or are exposed to other harsh conditions.

A robust technique suitable for clinical use emerged principally from the use of immunoperoxidase methods in conjunction with an initial incubation step in which tissue/cytological samples are exposed to pepsin and dilute hydrochloric acid. This initial incubation step renders nuclear histone H1 more accessible, and thereby more reliably reactive with mAb 12D11 in situ. Preliminary treatment of cells or tissues with detergents such as Triton X 100 (Sigma Chemical Co.) has also been found beneficial. Other aspects of this optimized histochemical method include the use of mAb 12D11 as a primary antibody, a commercially available biotinylated anti-mouse immunoglobulin secondary antibody, and a comercially available avidin-biotin amplification complex for horseradish peroxidase. Peroxidase-dependent immunoreactivity is visualized by the colored (brown) reaction product of diaminobenzidine. The improved method may be further refined for use with various immunochemical or enzymatic reagents, or optimized for use with diverse tissue types, with no more than routine experimentation.

Nuclear staining patterns obtained with this improved immunocyto/histochemical technique have, as a result of the studies reported herein, been recognized as characteristic respectively of terminally differentiated, benign proliferating or neoplastic cells. The nuclei of normal thyroid follicular cells (which are quiescent but have mitogenic potential) and of benign proliferating thyroid cells show a uniformly-distributed, smooth dark staining pattern. These results were observed for six out of seven individuals diagnosed by other means with benign follicular adenoma. In contrast, the nuclei of thyroid carcinoma cells exhibit a blotchy nonuniform staining pattern, ranging from dark areas to areas nearly devoid of 12D11 staining observed in a single cell nucleus. These results were observed for five out of five individuals diagnosed by other means with follicular carcinoma of the thyroid (four of whom showed completely nonuniform staining, and one of whom showed large areas of nonuniform staining), and for one of the above-mentioned seven individuals thought to have benign follicular adenoma. This last individual may therefore have actually presented clinically with a preinvasive thyroid cancer (i.e., during an interval between malignant change and the onset of invasion).

Success of the present improved immunocyto/histochemistry technique in the investigation of routinely processed clinical samples suggests a potential role for TAb 12D11 (PH1) which differs from the role of existing antibodies which are now commercially available for clinical use to assay the proliferation state of cells and tissue in surgically removed specimens. These antibodies, including reagents directed against Ki-67, cyclin-proliferating cell nuclear antigen (PCNA), and DNA polymerase alpha, require special tissue preparation, making already-routinely-prepared biopsy specimens inaccessible to analysis. In addition, histone H1 is among the most abundant cellular proteins, thus enhancing the sensitivity and reliability of mAb 12D11 detection.

To summarize, the effectiveness and reliability of monitoring shifts in the phosphorylation state of histone H1 for distinguishing between normal and neoplastic cells has been demonstrated in a variety of tissue types, and may be generally applicable to terminally differentiated cells or tissue. Most notable at present is the ability of mAb 12D11 (PH-1) to distinguish between malignant and benign thyroid nodules (follicular carcinoma versus adenoma). As described more fully below, this study suggests a means of improving the diagnosis and clinical management of patients with thyroid nodules. Based upon the clinical diagnostic studies reported herein, it is expected that the ability to visualize changes in histone H1 phosphorylation at the 12D11 epitope will be further applicable to unsolved problems in tumor diagnosis, tumor localization, early detection of tumors, and tumor prognostication. This will also permit the use of reagents such as mAb 12D11 in investigative studies such as retrospective survival studies of patients with tumors in which tissue and cell morphology alone fails to predict tumor aggressiveness or response to therapy.

Use of mAb 12D11 (PH-1) to Distinguish between Neoplastic and Benign Thyroid Nodules This study indicates that the clinical application of mAb 12D11 immunohistochemistry facilitates the unambiguous diagnosis of thyroid nodules potentially providing a means of triaging patients with thyroid enlargements to immediate surgery or to nonsurgical follow-up.

Thousands of individuals in the United States alone are found annually to have thyroid enlargement. The standard clinical protocol for determining the nature of these enlarged nodules includes fine needle aspiration (hereinafter FNA) of the thyroid, during which a biopsy specimen comprising thyroid cells are obtained from an individual by uptake with a fine needle, expelled onto surfaces suitable for microscopic evaluation (slides), stained with cytochemical dye according to standard techniques, and evaluated in a cytopathology laboratory. Upon visual inspection, about 5%–10% of these samples are found to contain neoplastic cells, whereupon the individual is treated surgically. Approximately 10–20% show unequivocally non-neoplastic changes, obviating the need for surgical excision. However, of the remaining samples, representing about 70–85% of the total, approximately one-half show indeterminate cytologic features which are common to both neoplastic and nonneoplastic enlargements. For this large class of individuals, immunocytochemistry with mAb 12D11 (PH-1) will provide the basis for counselling in favor of nonsurgical follow-up or immediate surgical resection.

Currently the major options available to individuals with thyroid nodules are twofold: they can either undergo immediate surgery, often for a nonneoplastic condition, in which case surgery is later determined to have been unnecessary. Alternatively, they may be placed on drug therapy which suppresses the pituitary secretion of thyroid stimulating hormone (TSH). This pituitary protein causes both proliferation and thyroid hormone secretion by thyroid cells. In some individuals, whose enlargement is due to benign nonneoplastic enlargement, removal of circulating TSH results in cessation of enlargement or shrinkage of the nodule over a period of three to six months. Those individuals whose nodules are actually malignant (follicular carcinoma), therefore are vulnerable to the additional risk of having an untreated tumor for up to six months, during which time the risk of metastasis exists.

The numerous advantages of the application of mAb 12D11 immunocytochemical staining, both to the individual and to the individual's caregivers, are readily apparent. The number of individuals subject to the anxiety and stress attendant to the possibility of having thyroid cancer is significantly reduced, a feature which also benefits the individual's primary care physician, endocrinologist and pathologist. Second, the risk that a latent thyroid carcinoma may spread or metastasize during suppressive therapy (which may last up to six months) is largely obviated. Third, incidences of unnecessary thyroid surgery will be reduced, even for individuals whose benign nodules do not shrink within six months of suppression. Conversely, individuals who presently opt for immediate surgery rather than accept the risks attendant to nonsurgical options will also have a sound basis on which to forego unnecessary surgery. From the caregiver's perspective, the present considerable overlap in cytopathologic criteria for distinguishing adenoma from carcinoma will be substantially reduced. Hence, the currently high degree of diagnostic uncertainty will be significantly diminished. For the surgical pathologist, this will provide an additional means of distinguishing benign from malignant thyroid follicular neoplasms.

Use of mAB b 12D11 to Assess Cervical Tissue for Cancerous or Precancerous Changes As noted previously, mAb 12D11 is additionally useful to inspect routine cervical specimens (PAP smears or cervical biopsies) for the presence of precancerous changes. PAP smears are samplings of cervical epithelial tissue, and in normal smears are largely comprised of terminally differentiated squamous epithelial cells whose nuclei are essentially negative for 12D11 reactivity. In normal samples, other cell types may also be present, including leukocytes and endocervical cells (from the lining of the uterine endocervical canal) that retain proliferative capacity. These are distinguishable visibly from squamous epithelial cells and the basal cells from which the squamous epithelia originates and is replenished. Basal cells, which are not terminally differentiated, are not normally found in PAP smears.

To assess samples for cancerous or precancerous changes, visual inspection is presently made of cytologically prepared PAP smears, with emphasis on the morphology of epithelial cells. In current practice, the appearance of the nuclei and cytoplasm of epithelial cells are used to assess whether full, normal differentiation has occurred, or whether cells originating from the basal layer and present at the cervical surface are cancerous or precancerous. Two types of precancerous changes have been characterized: the first is dysplasia, which is an impairment of the normal progress of cervical basal cells toward terminal differentiation into squamous epithelia. The second is condyloma, a wart-like precancerous change known to be of viral origin. Both dysplasia and condyloma may be induced by human papilloma viruses. The current method of analyzing PAP smears by visual inspection is susceptable to variability e.g., due to the differing interpretations or criteria applied by different operators or different processing laboratories.

Much of this variability and human error in the mechanics of screening slides may be obviated when PAP smears are assessed by the method of the present invention. Thus, even subtle dysplastic changes may be readily visualized by, e.g., immunohistochemical staining for the abnormal presence of histone H1 phosphorylated at the 12D11 epitope. Implementation of this technique would allow for at least the partial automation of routine PAP smear screening. Diagnosis of condyloma on surgical biopsy can also at times be problematic. Thus, the use of mAb 12D11 will help resolve the diagnosis in cases in which morphology alone is ambiguous.

Control of the Phosphorylation State of the 12D11 Epitope by Cell Cycle Associated Kinases cdc2/cdk2: Use of mAB 12D11 to Monitor cdc2/cdk2 Activity Recently, it has been demonstrated that the phosphorylation state of histone H1 at the 12D11 epitope is susceptible to regulation at least by the cell cycle associated kinases, cdc2/cdk2. These kinases are presently the subject of intensive investigation, as the possibility has recently emerged that they may represent the master kinase family in control of cell cycle regulation. Thus, cdc2/cdk2 is thought to be capable of directing whether a cell retains the capacity to initiate the cell cycle and undergo cell division (proliferation) or loses this capacity, thereby becoming terminally differentiated.

More specifically, cdc2/cdk2 status may underly the observations reported herein, which correlate 12D11 reactivity with the retention/reaquisition of proliferative capacity, and conversely the loss of 12D11 reactivity with the onset of terminal differentiation. Dedifferentiation may be more precisely cast as an inappropriate cellular return to the capacity to enter the cell cycle, or as an actual reentry into the cell cycle (proliferation). Due to the correlation between these cellular events and cancer, it is probable that cdc2/cdk2 will be the target of intensive anti-cancer drug development and drug screening efforts. It is accordingly envisioned that new mAb 12D11 (PH-1), together with the method for use of 12D11 to assess the proliferative capacity of cells and tissue disclosed herein, will provide excellent tools in support of these ongoing efforts to develop new anti-cancer, anti-cdc2/cdk2 therapeutic agents. That is, mAb 12D11 can be employed to indirectly assess cdc2/cdk2 activity by assessing the ability of cdc2\cdk2, in the presence of various candidate drug inhibitors, to phosphorylate or dephosphorylate histone H1 at the 12D11 site. Many specific embodiments and refinements of this application of mAb 12D11 are envisioned, and are considered within the scope of the present invention.

Practice of the invention disclosed herein will now be more precisely illustrated by the following Examples, which are not to be viewed as limiting in any way.

EXAMPLE 1

Production of Monoclonal Antibody 12D11 (PH-1)

The immunogen from which mAb 12D11 was generated was prepared as follows: a crude nuclear pellet was isolated from bovine brain: whole bovine brain was homogenized (Waring blender) in an equal volume buffer A (100 mM MES, pH 6.0., 0.5 mM $MgCl_2$, 5 mM mercaptoethanol, 1 mM EGTA, 5 $\mu$g/mL leupeptine, 0.2 mM phenylmethylsulfonyl fluoride, 0.5 mM benzamidine). After centrifugation (300×g, 4° C., 10 min), the pellet was discarded, and the supernatant was centrifuged again (5000×g, 4° C., 30 min). The second pellet was resuspended in an equal volume of 20 mM Tris (pH 7.5), and heated to 100° C. for 10 min. The suspension was then centrifuged (100,000×g, 4° C., 60 min), and the supernatant used as immunogen. This supernatant was also used at a protein concentration of 5 µg/mL for enzyme-linked immunosorbent assay (hereinafter ELISA) screening of the individual hybridoma supernatants.

Immunizations, generation of the hybridomas, and initial screening of the hybridoma supernatants by ELISA were performed using standard methods, as described in Kohtz et al. (1987), 104 J. CELL BIOL. 897–903. The hybridoma secreting mAb 12D11 was generated by the fusion of splenocytes from a mouse immunized with the bovine crude nuclear extract described above with Sp2/0 myeloma cells. Colonies initially positive in the ELISA were confirmed by immunofluorescence for subcellular localization as described below. Colonies exhibiting nuclear immunofluorescence were then assessed by Western blotting according to the method described below for reactivity with known nuclear antigens (including HMG 1, 2, 14, and 17; histones H1, H2A, H2B, H3, H4, and H5). Monoclonal antibody 12D11 was selected initially with this assay for its binding to histone H1, and was observed to bind exclusively to H1. The hybridoma cells secreting mAb 12D11 were subcloned twice by limiting dilution, at which stage uniform characteristics (monoclonality) of the secreted antibody were observed in all progeny.

The original scheme for generating mAb 12D11 was designed to identify any nuclear antigens that could be used to distinguish terminally differentiated from proliferating cells. As the identity of the antigen binding mAb 12D11 has been determined, a more direct method to generate functionally equivalent mAbs is possible: Purified calf thymus histone H1 is used as immunogen. Immunogenicity of histone H1 is greatly improved by covalent crosslinking to Keyhole limpet hemocyanin (KLH). This is accomplished by incubating 1 mg/ml histone H1 and 1 mg/ml KLH with 0.015% glutaraldehyde in phosphate buffered saline (PBS) for 1 hour (ambient temperature). The crosslinked reagent is dialyzed against PBS, and 1 mg/ml histone H1 is added to it prior to emulsification in complete Freund's adjuvant. Immunizations and boosts should range from 25 to 50 µg histone H1 (100 to 200 ul of 1:1 emulsion). Four weeks after primary immunization in complete Freund's adjuvant, boosts are started with emulsions in incomplete Freund's adjuvant. Three boosts at six week intervals each are required. Six weeks after the third boost, the animals are boosted intravenously with the antigen mixture in PBS alone. The next day, a second intravenous boost is performed. Three days hence, the spleens are removed, and fusion to myeloma cells and selection of hybridomas is performed using standard methods. The length of the immunization procedure requires that the mice not be more than 6–8 weeks of age at the primary immunization. A Balb/c mouse splenocyte fused to the Sp2/0 myeloma cell line produced mAb 12D11. Other fusion partner cell lines or strains may be used similarly.

In the alternate method, primary screening of the hybridoma supernatants is performed by ELISA using calf thymus histone H1 as an antigen. Those hybridoma clones producing monoclonal antibodies to calf thymus histone H1 are further tested for their functional identity with mAb 12D11 by determining that their binding to calf histone H1 is abrogated by bacterial alkaline phosphatase treatment, and that they do not bind histone H1 from skeletal muscle.

EXAMPLE 2

Subcellular Localization of Phosphorylated Histone H1 visualized in HUSK Cells by Immunofluorescence with mAb 12D11

Culture of Target Cells. Human fetal skeletal myoblasts (HUSK cells) were cultured on 35-mm culture plates as described by Feghali et al. (1992), 2 GENE EXPRESSION 49–58. HUSK cells were cultured in high mitogen medium, then switched to low mitogen medium for 48 h to induce differentiation. In this manner, two populations of cells were produced: terminally differentiated cells, which are mostly multinucleated (syncitia) and express sarcomeric proteins, and quiescent mononuclear cells which do not express sarcomeric proteins.

Culture of Hybridomas. Hybridoma cells secreting mAb 12D11 were grown in RPMI medium (GIBCO) containing 10% fetal bovine serum (HyClone), minimum Eagle's medium nonessential amino acids (GIBCO), minimum Eagle's medium vitamins (GIBCO), 1 mM sodium pyruvate, 100 µg/mL L-glutamine, and 100 µg/mL gentamicin. Culture supernatants were used full strength (undiluted), but were supplemented with 20 mM HEPES, pH 7.4.

Reference Monoclonal Antibody. Monoclonal antibody MF-20, which binds to sarcomeric myosin heavy chain (hereinafter sMHC; Bader et al. (1982), 95 J. CELL. BIOL. 763–770), was grown as an ascites tumor in nude mice. The ascites fluid was diluted 1:1000 in TBS supplemented with 5% horse serum, 5% nonfat dry milk, and 0.2% Tween 20 for both Western blotting and immunofluorescence studies.

Immunofluorescence Method. Target cells were washed twice at ambient temperature with phosphate-buffered saline (PBS: 100 mM $Na_2HPO_4$/$NaH_2PO_4$ pH 7.4, 154 mM NaCl), fixed with freshly made 3.7% paraformaldehyde in PBS (15 min). Target cells were then treated with 0.2% Triton X-100 in PBS, washed once with PBS, then saturated for 30 min with 10% horse serum (EIA grade, GIBCO), all at ambient temperature. Hybridoma supernatant from mAb 12D11 was applied directly to the cells, then incubated for 1 h at 37° C. The cells were then washed twice, and incubated with fluorescein isothiocyanate-conjugated goat anti-mouse (Boehringer Mannheim) diluted 1:50 in 0.1% bovine serum albumin-supplemented PBS, 45 min at 37° C. The cells were then washed three times with PBS and viewed on an inverted Nikon Diaphot fluorescence microscope, by phase microscopy, and for fluorescence through the fluorescein channel and the Hoechst channel for DNA (Hoechst dye reveals all nuclei).

Results. Undifferentiated HUSK cells were stained with mAb 12D11 and Hoechst dye. The two patterns were found to be indistinguishable. Thus, HUSK myoblasts in high mitogen medium displayed positive nuclear staining with mAb 12D11.

Differentiated HUSK cells were also stained with mAb 12D11 and Hoeschst dye. A striking effect was observed: differentiated cells, as determined from the presence of multinucleated syncytia, were negative for staining by mAb 12D11, whereas quiescent mononuclear cells were positive for nuclear staining with mAb 12D11. That is, differentiated multinucleated myofibers lacked 12D11$^+$ histone H1, whereas undifferentiated, quiescent mononuclear cells retained 12D11$^+$ histone H1.

When stained with a mixture of mAbs 12D11 and MF-20 (as reference; an anti-sMHC mAb), a differentiated multinucleated myofiber showed cytoplasmic MF-20 staining, whereas an undifferentiated, quiescent mononuclear cell in the same field of view showed a punctate pattern of 12D11 staining. In other words, the loss of staining by mAb 12D11 was not associated merely with the formation of syncytia but rather with the expression of sarcomeric proteins. Several independent controls have shown that mAb MF-20 does not stain the nuclear compartment and mAb 12D11 does not stain cytoplasmic compartment.

In another field of view, a differentiated mononuclear myocyte and undifferentiated quiescent mononuclear cells were observed following staining with a mixture of mAbs 12D11 and MF-20. Here, mAb MF-20 revealed sarcomeric striations in the differentiated cell, whereas the presence of nuclear staining by mAb 12D11 was found only in the undifferentiated cells.

Thus, differentiated mononuclear myocytes expressing sarcomeric myosin heavy chain also are negative for staining by 12D11. Together, these data indicate that loss of 12D11+ histone H1 is associated with myogenic differentiation and not with mitogenic arrest of myoblasts in the absence of differentiation.

It should be noted that only human, canine, and bovine cell lines produced strong immunofluorescent signals with mAb 12D11, whereas rodent cell lines, despite displaying impressive binding when assessed by Western blotting (see below), produced weak immunofluorescence signals.

EXAMPLE 3

Monoclonal Antibody 12D11 was shown by Western Blotting to Bind to a Slow-Migrating Subset of Histone H1

Electrophoretic Resolution of Histone H1. Bovine thymus histone H1 (10 μg/lane) purified according to standard methods (see below) was solubilized in an equal volume of sample buffer (100 mM Tris, pH 6.8; 2% SDS (w/v), 0.25% phenol red (w/v), 10% glycerol, 5% (v/v) mercaptoethanol), heated briefly to 100° C., and resolved by sodium dodecyl sulfate-polyacrylamide gel electrophoresis (hereinafter SDS-PAGE) on a 15% polyacrylamide gel using the discontinuous buffer system described initially by Laemmli (1970), 227 NATURE 680–685. A first lane containing resolved histone H1 was excised from the gel, fixed with 10% acetic acid, 25% methanol, and stained for total protein with Coomassie Brilliant Blue (Sigma). Other lanes from the same gel were transferred to nitrocellulose as described below.

Western Blotting Procedures. Resolved proteins on electrophoresis gels were transferred to nitrocellulose for Western blotting according to procedures recommended by Bio-Rad, the manufacturer of the Trans-Blot transfer apparatus employed. Transfer efficiency was monitored by the appearance on the nitrocellulose sheet of prestained marker proteins run on a separate lane of the gel.

After protein transfer, nitrocellulose sheets containing blotted proteins were treated with 10% acetic acid, 25% isopropanol for 10 min, then washed with several changes of water. The sheets were then incubated with gentle rotary shaking for 8–18 h (4° C.) in TBS. The sheets were then incubated 8–18 h (4° C.) in TBS supplemented with 10% Carnation nonfat dry milk. The sheets were washed with TBS containing 0.2% Tween 20 and incubated overnight with primary antibody (mAb 12D11, from culture supernatants diluted 1:2.5 in Tris-buffered saline (TBS: 20 mM Tris, pH 7.5, 100 mM Nacl) containing 0.2% Tween 20 (Sigma)). The sheets were then washed twice with TBS containing 0.2% Tween 20 and incubated overnight (4° C.) with 5 μCi $^{125}$1-labeled rabbit anti-mouse IgG (Du Pont-New England Nuclear) in the buffer described above for mAb MF-20 (TBS supplemented with 5% horse serum, 5% nonfat dry milk, and 0.2% Tween 20), supplemented additionally with 0.5M NaCl. The blots were washed (with shaking) twice (4° C., 20 min each) with TBS supplemented with 0.2% Tween 20 and 0.5M NaCl, once (4° C.) with TBS supplemented with 0.2% Tween 20, and once (ambient temperature) with TBS, then dried and exposed to Kodak XAR-5 film using a Du Pont Lightening plus intensifying screen.

Results. mAb 12D11 was shown to react with a form of histone H1 that migrates slower than the bulk of H1 during SDS-PAGE. The relationship between mAb 12D11+ H1 and bulk histone H1 was visualized by Amido Black staining of the blot according to standard methods.

EXAMPLE 4

The 12D11+ Subset of Histone H1 is Antigenically Distinguishable from Bulk Histone H1 on the Basis of Phosphorylation Purification of Histone H1. Histone H1 was purified as previously described (Fasy et al. (1979), 564 BIOCHEM. BIOPHYS. ACTA 322–334; Monestier et al. (1989), 26 MOL. IMMUNOL. 749–758) from bovine thymus, human placenta, and human skeletal muscle (obtained at autopsy).

Phosphatase Treatment of Histone H1. Phosphatase reactions were performed with purified H1 from human placenta in 10 mM Tris, pH 8.3, 1 mM $MgCL_2$, 1 mM $ZnCl_2$. Samples were incubated with 0.7 unit of bacterial alkaline phosphatase for 45 min (37° C.). An additional 1.4 units were then added, and the mixture was then incubated for another 45 min. Sham reactions were performed in parallel without added enzyme. The histone H1 was then isolated by precipitating the bacterial alkaline phosphatase with an equal volume of cold 10% perchloric acid and pelleting the precipitate in a microcentrifuge at 13,000 rpm for 10 min at 4° C. The supernatant was collected and either neutralized with 2M Tris, pH 8, or 12N HCl was added at a dilution of 1:50 to the sample and the histone was precipitated with 10 volumes of acetone.

Reference Monoclonal Antibody. Monoclonal antibody MRA12, an IgG2a that binds generically to histone H1 (Monestier et al. (1989), 26 MOL. IMMUNOL. 749–758), was purified, lyophilized, and provided by M. Monestier. It was used at a final concentration of 5 μg/mL in the same buffer as MF-20, above.

Electrophoretic resolution and Western blotting. Procedures were as described above in Example 3. In this study, purified human placental histone H1 (2.5 μg/lane) was treated with bacterial alkaline phosphatase or sham-treated, then repurified. A first set of samples were resolved by SDS-PAGE and stained with Coomassie Brilliant Blue. A second set were analyzed by Western blot with mAb 12D11 as the primary antibody, and a third set were analyzed by Western blot with reference mAb MRA12 as the primary antibody.

Results. In each set of samples, lanes with untreated histone H1 produced narrower bands because of the higher glycerol content of their samples. Bacterial alkaline phosphatase treatment of H1 eliminated all reactivity with mAb 12D11, without affecting the generic reactivity of mAb MRA 12 with the bulk histone H1 doublet. These results show that mAb 12D11 reacts specifically with a phosphorylated subset of histone H1.

In separate studies, it has been shown that the 12D11 epitope itself contains or is intimately associated with the phosphorylation site. Treatment of fixed cultured cells (prepared generally as described above in Example 1) with bacterial alkaline phosphatase also abolished reactivity with mAb 12D11. These corroborative results, obtained with either electrophorectically linearized or covalently crosslinked (fixed) histone H1, are consistent with the view that the 12D11 epitope is a contiguous amino acid sequence spanning or immediately adjacent to the phosphorylation site, and not a conformational epitope or a distal contiguous amino acid sequence revealed by conformational change associated with phosphorylation.

EXAMPLE 5

The 12D11$^+$ Histone H1 Subset is not Present in Histone H1 Purified from Terminally Differentiated Cells Purification of Histone H1. Histone H1 was purified from human adult skeletal muscle and placenta, as noted above in Example 4.

Electrophoresis and Western Blotting. Two sets of samples (skeletal muscle and placenta, 2.5 μg/lane) were prepared and subjected to SDS-PAGE on 18% gels as described above in Example 3. One set was stained with Coomassie Brilliant Blue, while the other was analyzed by Western blot with mAb 12D11.

Results. The phosphorylated subset of histone H1 recognized by mAb 12D11 (12D11$^+$ histone H1) displayed variable expression in different cell lines and tissue. For example, preparations of bovine thymus (Example 3), bovine brain (Example 2), and human placenta all produced positive signals in Western blots with mAb 12D11. In contrast, preparations of histone H1 from adult human skeletal muscle did not contain detectable 12D11$^+$ histone H1. Skeletal muscle histone H1 does, however, contain a large amount of histone H1° which migrates as a single band just ahead of the usual H1 doublet.

EXAMPLE 6

12D11+ H1 is Lost Upon Cell Differentiation

Target Cell Culture. C2C12 myoblasts (Blau et al. (1983), 22 CELL 1171–1180) were grown on 35-mm culture plates in Dulbecco's modified Eagle's medium supplemented with 15% fetal bovine serum (HyClone), 1% chick embryo extract (GIBCO), minimum Eagle's medium nonessential amino acids (GIBCO), minimum Eagle's medium vitamins (GIBCO), 1 mM sodium pyruvate, 100 μg/mL L-glutamine, and 100 μg/mL gentamicin. To induce differentiation, similar medium was used in which fetal bovine serum and embryo extract were replaced by 4% horse serum.

HUSK cells (Feghali et al. (1992), 2 GENE EXPRESSION 49–58) were cultured and induced to differentiate as described above in Example 2.

Timecourse profiles were constructed for tracking the differentiation of each cell type (HUSK and C2C12 myoblasts) by harvesting samples of each culture from high mitogen medium (baseline; 0 h), and at several intervals over a period of hours postinduction (i.e., following the switch to low mitogen medium to induce differentiation). Equal cell numbers (number of nuclei were considered in fused cells) were used per timecourse sample, and timecourse studies were always performed sequentially with identical starting cultures.

Preparation of Cell Lysates. Cell lysates for SDS-PAGE were generated by washing monolayers with PBS and adding electrophoresis sample buffer directly to the tissue culture plates harvested at each timepoints.

SDS-PAGE. Cell lysates were heated at 100° C. prior to electrophoresis on either 9% (for myosin heavy chain) or 18% polyacrylamide gels (for histone H1) using the discontinuous buffer system of Laemmli (1970), 227 NATURE 680–685, as described above in Example 3. Each lysate was inspected for anomalies by SDS-PAGE and Coomassie stain before being used for Western blotting studies.

Western blotting. The procedure described above in Example 3 was followed, using as primary antibodies, either mAb 12D11 (to assess 12D11$^+$ H1) or reference mAb MF-20 (to assess sarcomeric myosin heavy chain (sMHC) protein expression as a marker for myogenic differentiation. Bader et al. (1982), 95 J. CELL. BIOL. 763–770. The onset of sMHC expression coincides with the formation of syncytia 24–96 h after myoblasts are switched to low mitogen medium). Microdensitometry scans, schematically illustrated in FIG. 1, were also obtained from each blot.

Figure 1B:
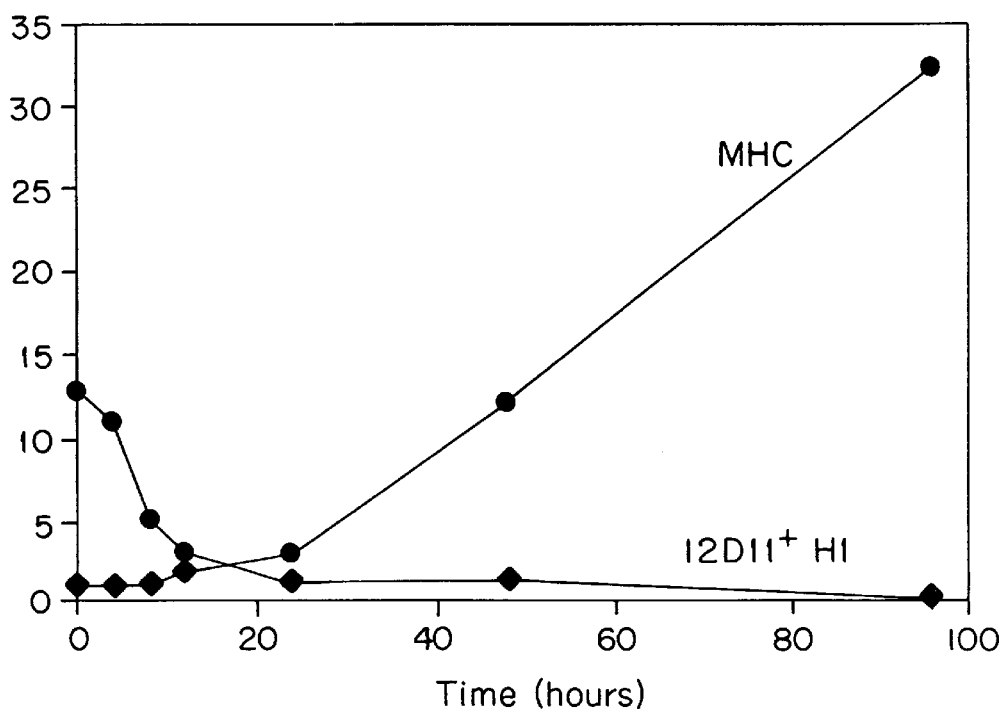
FIG. 1B is a schematic illustration of a microdensitometry scan of Western-blotted timecourse samples assessing the onset of differentiation in C2C12 cells. MHC and $12D11^+$ H1 are as in FIG. 1A.

Results. In a typical experiment, HUSK cells produced high levels of sMHC after 96 h in low mitogen medium, and C2C12 myoblasts produced high levels after 48 h. The same set of samples was immunoblotted with mAb 12D11, revealing that 12D11$^+$ histone H1 expression started to diminish within 8 (C2C12) to 24 (HUSK) h after the cells were switched to low mitogen medium. Corresponding to the induction of syncytia formation and high level sMHC expression, 12D11$^+$ histone H1 expression dropped to its lowest levels 48–96 h after switching the cells to low mitogen medium (FIG. 1). These studies have been repeated several times, and the time period from switching the cells to low mitogen medium to the onset of differentiation varied from 18 to 96 h. Several factors produce this expected variability, including cell density and variations between different preparations of medium. In all cases, the onset of differentiation occurred as 12D11$^+$ histone H1 reached a minimum.

EXAMPLE 7

Monoclonal Antibody 12D11 (PH-1) Distinguishes Between Quiescence and Differentiation Target Cell Culture. When cultured at confluence in low mitogen medium supplemented with TGF-β, skeletal myoblasts withdraw from the cell cycle (Olson et al. (1986), 103 J. CELL BIOL. 1799–1805; Massague et al. (1986), 83 PROC. NATL. ACAD. SCI. U.S.A. 8206–8210), but neither form syncytia nor express biochemical markers of differentiation such as sMHC. Myoblasts cultured in the presence of TGF-β maintain the ability to differentiate after the factor is removed. Vaidya et al. (1989), 9 MOL. CELL BIOL. 3516–3579. Thus, HUSK and C2C12 myoblasts were cultured as myoblasts in high mitogen medium, then switched at confluence to low mitogen medium, or to low mitogen medium supplemented with TGF-β. Cell culture and differentiation induction were as described above in Example 6. TGF-β was purchased from R & D Systems and used at a concentration of 5 ng/mL in 4% horse serum medium. Cells were maintained in culture for 72 h postinduction.

Preparation of Cell Lysates: SDS-PAGE Resolution. Whole cell homogenates (representing equal numbers of cells or cell nuclei in fused cells) were prepared and resolved by SDS-PAGE as described in Example 6.

Western blotting. The blotting procedures described in Example 6 were followed, using either mAb 12D11 or reference mAb MF-20.

Results. Inhibition of HUSK and C2C12 myoblast differentiation by TGF-β was evident visually from a lack of syncytia in the cultures, a lack of troponin I mRNA accumulation (assessed by standard methods), and in Western blots from the absence of sMHC expression after 72 h.

Parallel flasks of cells cultured in low mitogen medium not supplemented with TGF-β differentiated normally, and expressed sMHC. Moreover, in the presence of low mitogen medium supplemented with TFG-β, differentiation was inhibited without a concommitant reduction in the level of MyoD1 mRNA (as assessed by standard methods). Western blots with mAb 12D11 revealed that 12D11+ histone H1 levels in confluent quiescent myoblasts cultured with TGF-β were comparable to those observed in proliferating myoblasts. The amount of 12D11+ histone H1 in differentiated cultures generated in parallel approached undetectable levels.

Replacement of TGF-β supplemented medium in differentiation-inhibited cultures with low mitogen medium lacking TGF-β resulted in the induction of sMHC expression in 48 h, accompanied by a corresponding loss of 12D11+ histone H1. The data show that TGF-β inhibits differentiation of myoblasts while sustaining histone H1 phosphorylation at the 12D11 epitope. Thus, TGF-β cultured myoblasts are quiescent but not terminally differentiated. That is, the potential to proliferate has been retained in these cells.

Equivalents

Those skilled in the art will recognize, or be able to ascertain using no more than routine experimentation, many equivalents to the specific embodiments of the invention described herein. These and all other such equivalents are intended to be encompassed by the following claims.

I claim:

1. A monoclonal antibody that binds to phosphorylated histone H1 and not to nonphosphorylated histone H1.

2. A monoclonal antibody that binds to histone H1 at a phosphorylation site when the phosphorylation site is phosphorylated and does not bind to histone H1 at the phosphorylation site when the phosphorylation site is not phosphorylated.

3. A monclonal antibody of claim 2 that binds to histone H1 of human origin.

4. A monoclonal antibody of claim 3 that binds to human histone H1 in an enzyme linked immunosorbent assay or in a radioimmunoassay.

5. A monoclonal antibody of claim 3 that binds to Western-blotted human histone H1.

6. A monoclonal antibody of claim 3 that binds to slot- or dot-blotted human histone H1.

7. A monoclonal antibody of claim 3 that binds to human histone H1 in cells or tissue.

8. A monoclonal antibody of claim 3 that binds to human histone H1 in situ in cells or tissue prepared from a surgically resected pathology specimen.

9. A monoclonal antibody of claim 3 that binds to human histone H1 in situ in cells or tissue prepared from a presurgical biopsy specimen.

10. A monoclonal antibody of claim 7, the binding of which is detectable by immunofluorescence.

11. A monoclonal antibody of claim 7, the binding of which is detectable by immunohistochemistry.

12. A detectably labeled monoclonal antibody of claim 3.

13. An antibody that binds to phosphorylated histone H1 and not to nonphosphorylated histone H1.

14. An antibody that binds to histone H1 at a phosphorylation site when the phosphorylation site is phosphorylated and does not bind to histone H1 at the phosphorylation site when the phosphorylation site is not phosphorylated.

* * * * *